United States Patent [19]
Grodzins et al.

[11] Patent Number: 5,461,654
[45] Date of Patent: Oct. 24, 1995

[54] X-RAY FLUORESCENCE DETECTOR

[76] Inventors: Lee Grodzins, 14 Stratham Rd., Lexington, Mass. 02173; Charles G. Parsons, P.O. Box 430, Nutting Lake, Mass. 01865

[21] Appl. No.: 142,217

[22] Filed: Oct. 25, 1993

Related U.S. Application Data

[63] Continuation-in-part of Ser. No. 96,160, Jul. 23, 1993, which is a continuation-in-part of Ser. No. 863,807, Apr. 7, 1992, Pat. No. 5,274,688.

[51] Int. Cl.$^6$ .................................................. G01N 23/223
[52] U.S. Cl. ................... 378/45; 378/44; 378/50
[58] Field of Search ........................... 378/44, 45, 58, 378/53, 88

[56] References Cited

U.S. PATENT DOCUMENTS 4,845,729  7/1989  Rosen et al. ........................ 378/45
5,274,688  12/1993  Grodzins ............................ 378/45

*Primary Examiner*—David P. Porta

[57] ABSTRACT

A new type of x-ray fluorescence detector is disclosed that utilizes the measured intensities of fluorescent $L_\alpha$ and $L_\beta$ x-rays, or $K_\alpha$ and $K_\beta$ x-rays of a target element, to determine the absorption of the covering layer over the target element, without a priori knowledge of the concentration of the target element. The detector uses a source of initiating photons whose energy is in a specific range, a detector of the characteristic lead L or K x-rays with sufficient energy resolution to measure the intensities of the $L_\alpha$ and $L_\beta$ rays separately. The detector will, in a rapid, non-destructive manner, provide information as to the depth that the lead paint is beneath the surface. This information is of use to those who mitigate a lead-paint infested area.

7 Claims, 5 Drawing Sheets

X-RAY FLUORESCENCE DETECTOR

This application is a continuation in part of pending application Ser. No. 08/096,160 filed on Jul. 23, 1993, which is a continuation in part of Ser. No. 07/863,807 filed on Apr. 7, 1992, U.S. Pat. No. 5,274,688.

BACKGROUND OF THE INVENTION

1. Field of the Invention

This invention is in the field of detectors, for example, lead detectors using x-ray fluorescence (XRF).

2. Description of the Prior Art

Many studies have shown that lead is a poison especially harmful to children. The Environmental Protection Agency and HUD have determined that lead paint in houses is a root cause of the poisoning of children and have recommended its elimination. Lead paint was in common use throughout most of the country until the 1960's; it was not completely phased off the market until the 1970's. Now States, including Massachusetts, have passed laws requiring its removal from residential dwellings. A central problem to a stronger effort to eradicate the lead paint hazard is the difficulty and expense of testing for the low lead concentrations considered dangerous.

The problem has been thoroughly discussed in publications from the National Institute of Standards and Technology. Two recent review publications from the NIST are particularly relevant. *Methods for Measuring Lead Concentrations in Paint Films* by M. E. McKnight, W. E. Byrd, W. E. Roberts and E. S. Lagergren, U.S. Department of Commerce, National Institute of Standards and Technology, 1989, NISTR 89 4209, gives is a comprehensive examination of the methods for measuring lead concentrations in paint films. *Screening Procedures for Detecting Lead in Existing Paint Films* by M. E. McKnight and W. E. Byrd, U.S. Department of Commerce, National Institute of Standards and Technology, 1990, NISTR 89-4044, is a literature survey of the screening procedures for detecting lead in existing paint films. Three general methods for finding lead paint on surfaces are available: chemical tests, absorption spectroscopy and x-ray fluorescence.

1) The chemical tests make use of the fact that the color of certain chemicals will change when exposed to lead. To use the technique, the inspector places the chemical on a chip of the paint, or places the chemical in a cut made through the paint on the wall. Chemical tests are inexpensive, a home-test kit can be purchased for less than 10 dollars. Chemical tests are not recommended by the various regulatory bodies, however, because of their many drawbacks: they are destructive of the surface, the tests are qualitative rather than quantitative, the tests cannot be easily repeated, and the tests do not result in a hard-copy output for the record.

2) Absorption spectroscopy is a quantitative, sensitive technique but requires that paint samples be taken to a laboratory to be analyzed by highly trained technicians using complex and costly spectrometers.

3) X-ray fluorescence is the preferred technique for field use. In principle, it obviates all of the drawbacks of the other two methods. The tests can be done with a portable instrument in a non-destructive, repeatable and quantitative manner so as to produce a validated, hard-copy output at the test point. X-ray fluorescence analysis, which is well-described in the literature, such as *X-ray Fluorescence Spectrometry* by Ron Jenkins, John Wiley & Sons publishers, 1988, makes use of the fact that one can determine the presence and amount of an element by measuring its characteristic x-rays emitted when the atoms of the material are excited by initiating photons. The XRF methods based on K x-ray detection make use of the fact that the innermost electrons of the lead atom, the so-called K-shell electrons, are bound to the nucleus with an energy of ~88.005 keV. When a photon with energy greater than 88.005 keV strikes the lead atom, there is a probability that the K-electron will be ejected leaving a vacancy in the K-shell. That vacancy is quickly filled by one of the outer electrons, producing a spectrum of K x-rays unique to lead. The principal K x-ray lines are: $K_{\alpha_1}$=74.96 keV (most intense), $K_{\alpha_2}$=72.79 keV, $K_{\beta_1}$= 84.922 keV and $K_{\beta_2}$=87.35 keV. X-ray-fluorescent (XRF) lead detectors on the market today use the 122 keV gamma rays from $^{57}$Co sources, with a half-life of 271.8 days, to photo-electrically excite the lead, and measure the lead K x-rays emitted from the sample surface, using an appropriate detector. Unfortunately, present x-ray fluorescent instruments are expensive, costing between $8,000 and $20,000, and the radioactive sources must be replaced, at least every year, at a cost between $1,500 and $3,500, depending on the strength needed. Since present instruments require a minimum of 20 seconds to make a single measurement of 1 mg/cm$^2$ of lead, and three measurements are required for each test location, a complete lead paint analysis takes several hours of an inspector's time, and can cost more than all other home inspections combined.

The instruments on the market today have difficulty with false alarms, as emphasized by McKnight et al in NISTR 89 4209, due in part to the fact that the measured signal depends on the substratum under the paint. Thus, the count rate in the K x-ray window changes as the detector scans the walls of the room, even in the absence of lead. These substratum effects are well known confounders for present XRF portable paint analyzers.

The NISTR 89-4044 publication by McKnight and Byrd list six criteria for a lead screening test. "The procedures should be: 1) capable of detecting lead concentrations of 1 mg/cm$^2$, 2) non-hazardous, 3) suitable for use as a non-destructive or minimally destructive field method, 4) suitable for use by non-technical personnel, 5) sufficiently reliable, precise and accurate and 6) rapid." The conclusion of the NISTR report (page 10) is that "Based upon the literature, no screening methods were found for detecting lead in paint that meet all the criteria.."

The patent application describes a new method, using L x-rays for measuring lead concentrations, that meets all six of the McKnight and Byrd criteria. An additional feature of the invention, not stressed in the prior applications, is that the L x-ray technique gives a measure of how much non-lead paint is covering the lead paint layer. The present invention describes the utilization of the novel L x-ray algorithms to quantify the non-lead paint layers above the lead-paint layers. The use of the invention for this purpose is important since a fast, inexpensive, reliable indicator of the depth of the lead paint beneath layers of non-lead paint strongly affects the economics of mitigating a lead-paint infested area. If the lead paint is buried beneath layers of well-bonded, non-lead paint, then the leaded paint presents a much reduced health risk. At this time there is no quantitative, non-destructive measure of the depth of the lead paint beneath the surface. The present invention gives the areal density of the lead paint and simultaneously the absorption of the cover layer. The absorption of the cover layer is a good index of the cover thickness.

The use of L x-rays to measure the lead in surfaces is well known but poorly regarded. The comprehensive NISTR 89-4209 report dismisses the method by citing only one reference, a paper by S. D. Rasberry, *Investigation of Portable X-ray Fluorescence Analyzers for Determining Lead on Painted Surfaces,* Applied Spectroscopy, 27, pp 102–108 (1973). Rasberry discusses L x-ray methods in only a few sentences on page 103 of the reference: "It is important to note that only analyzers which detect a K x-ray line of lead should be used in searching for lead in wall paint. The L x-ray lines are so low in energy that they are readily absorbed in any overlayers of non-lead paint, leading to probable false-negative results whenever several layers of paint are superimposed." Rasberry does, however, acknowledge the sensitivity of the technique in the next sentence of the reference: "Analyzers which detect L-lines are quite sensitive for lead in single layers of paint, but their use should be restricted to newly made and painted items such as toys or furniture." Rasberry's conclusions were not based on empirical data, yet have had considerable influence on the field; his conclusion is still cited by the experts almost twenty years later. In fact, as we will show, the L x-ray technique can be used to quantitatively determine low-levels of lead concentration under the 10 layers of $TiO_2$ paint that Rasberry uses as his maximum test thickness. We also note that we have been unable to find any reference, such as Jenkins cited above, that makes use of the unique properties of the absorption of L x-rays that is our special discovery and which allows the concentration of heavy elements such as lead to be determined in the field, independent of the thickness and nature of the covering layers of non-lead paint.

SUMMARY OF THE INVENTION

This invention uses the absolute concentration of the $L_\alpha$ and $L_\beta$ x-rays of a heavy element to determine the absolute areal density of the heavy element independent of the thickness and nature of the material covering the heavy element; the invention also yields, at the same time, the amount by which the covering layers absorb the L x-rays. The focus of this invention is on the measurement of lead in lead paint that may be covered by layers of non-leaded paint, but we emphasize that the method can be applied to the detection and measurement of all near-surface elements in which the intensities of at least two of the L x-rays, e.g., the $L_\alpha$ and $L_\beta$ x-rays, can be determined. We further assume that the L x-rays are induced by photons, that is, the invention will generally be used in the x-ray or gamma-ray fluorescence mode, but we emphasize that the method can be applied if the L x-rays are induced by electrons or heavy ions. For convenience, the invention will be called LXF, for L x-ray fluorescence. The fluorescing photons, which we will sometimes refer to as the initiating or inducing or fluorescing radiation or the initiating or inducing or fluorescing photons, can be from a radioactive source or from an x-ray tube.

It is important to keep in mind that the task of a lead-paint detector is to detect the maximum allowable lead concentration, i.e. 1 mg/cm$^2$. The measurement of a lead signal gives its minimum concentration. The inclusion of absorption by the covering layers of non-lead paint can only increase the value, it can never decrease it. Thus, the detection of an unambiguous lead signal greater than allowed mandates the total removal of the paint, at a considerable cost. There is considerable interest in relaxing the requirements for immediate removal of the lead-paint if the lead-painted surfaces are sufficiently well covered by non-leaded paint of good integrity.

In the following paragraphs we consider the application of LXF to near-surface lead where the absorption from covering paint is negligible. We next consider the measurement of lead beneath a thickness of non-lead paint. We prove the central point of this invention that the absolute magnitudes of the $L_\alpha$ and $L_\beta$ x-ray intensities observed from the surface being analyzed gives the absolute concentration of the lead, independent of the thickness or nature of the paint or material covering the lead. The inducing photons that are incoherently (Compton) scattered by the material under analysis gives the absolute measure of the background under the lead $L_\alpha$ and $L_\beta$ peaks in the detector, an important piece of information, especially when the lead concentrations are very low. Finally, we note that certain paints, such as zinc-based and copper-based, which strongly absorb the lead L x-rays, are themselves highly fluorescent and yield distinct and easily observable x-ray peaks that allow the method to correct for the absorption due to these elements.

In the preferred embodiment, the invention uses as the initiating radiation the K x-ray spectrum emitted in the radioactive decay of $^{109}$Cd. The radiations from this source will be used to describe the invention; other choices for the initiating radiation will be considered separately. In the preferred embodiment, the invention uses a silicon PIN diode as the detector of the radiations emitted from the surface of the sample and the silicon PIN diode will be used to describe the invention; other choices for detectors are considered separately. In the preferred embodiment of the invention, the geometry of source and detector can be as shown in FIG. 1 in which the detector 5 detects radiations from the surface 1 and the angle between the initiating photons 6 and the detected photons 7 ranges from less than 90° to almost 180°. The spectrum of detected radiations, which include the fluorescent x-rays, the incoherent and the coherent scattering, will be called, for convenience, the back-directed radiation spectrum, but we emphasize that the angle between the initiating and detected photons is not restricted in this invention, apart from the practical need to shield the detector from the direct radiations from the source.

FIG. 1 shows the principal elements of the invention. A source 3 emits initiating photons 6 that, with the safety cover 11 off, impinge on test object 12 that consists of a surface layer 1 of material such as coats of paint, that is on a substratum 2 of material such as wood. The detector 5 detects a spectrum of photons 7 that consist of fluorescent x-rays, and photons from the initiating source that are scattered by the sample 12. A shield 4 isolates the detector 5 from the direct radiations from the source 3. The signals from the detector 5 are amplified by electronic means 8, processed by an appropriate signal processor means 9 and the results presented in the appropriate output means 10.

FIG. 2 shows the principal features of the back-detected spectrum 27 from surface lead on a substrate of wood and 28 from the wood substrate only. The spectra in this and other figures were obtained in a geometry similar to that of FIG. 1. The initiating radiations were the K x-ray photons from a $^{109}$Cd source. $^{109}$Cd, which lives 463.2 days, emits slightly more than 1 K x-ray of silver per decay. The 22.1 keV $K_\alpha$ lines make up 80% of the x-ray strength; the remainder is mostly in the $K_\beta$ lines at 25.0 keV. (We will only consider the 22.1 keV x-rays in the calculations below; the 25 keV component makes the invention about 15% more effective than the estimates presented here.) The detector was a PIN silicon diode detector having an energy resolution of about 1.5 keV (full-width-at-half-maximum). The target was a standard supplied to us by the Massachusetts Department of Public Health; half of one surface was painted with a lead paint standard containing 1.6 mg/cm² of lead, the other half was painted with a non-lead paint.

The spectrum 27 has three general features: the L x-ray spectrum of the lead, the incoherent (Compton) scattering of the initiating radiation, and a background. The L x-ray spectrum from lead is quite complex in its details but most of the prominent x-rays fall into three distinct energy groups that most detectors useful for field work cannot further resolve. These are the $L_\alpha$ x-rays at about 10.5 keV, 21 the $L_\beta$ x-rays at about 12.6 keV, 22 and the $L_\gamma$ x-rays at about 15 keV, 23. The $L_\alpha$ and $L_\beta$ x-rays have approximately equal intrinsic intensities (the $L_\beta$ x-rays being more dominant), while the $L_\gamma$ x-rays make up about 10% of the total L x-ray spectrum. (The strength of the $L_\alpha$ peak 21 is stronger than the intensity of the $L_\beta$ peak 22 in FIG. 2 because the efficiency of the detector strongly favored the lower energy line.) The intensity of the $L_\gamma$ x-rays 23 becomes important in the analysis when the absorption of the $L_\alpha$ and $L_\beta$ x-rays in the covering layers is so great that the intensity of the $L_\alpha$ x-rays cannot be accurately determined. The spectrum of incoherent scattered radiation consists of two peaks, a strong line at a mean energy of about 20.5 keV 24 coming from the Compton scattering through about 135° of the 22.1 keV $K_\alpha$ line of $^{109}$Ag, and a weak line at about 23 keV 25 coming from the Compton scattering of the 25 keV $K_\beta$ line of $^{109}$Ag. The latter peak, while easily observed in the spectrum of FIG. 2, has relatively low intensity and will not be further discussed. We note that the Compton peak position is not strongly dependent on the angle of scattering. For example, the energy of the 22.1 keV photons that are Compton scattered through 90° is 21.2 keV, only 5% higher that the 20.3 keV photons observed at 180° scattering. Thus Compton scattering over a broad range of angles still results in an effective single peak with a mean energy between 20.3 and 21.2 keV. The intrinsic noise of the detector 5 and the pre-amplifier 8 are the main contributors to the widths of the peaks 21, 22, 23, 24 and 25. The background 26 under the L x-ray peaks 21 and 22 comes from the detector response of the higher energy photons, principally, 24 and 25. The background 26 must be accounted for in the detection of lead since its magnitude can be comparable or greater than the magnitude of the lead signal.

The testing of paint on wood is an example of the application of this invention to the measurement of the concentration of a target element, i.e. lead, painted on a substrate, for example, wood, the paint being covered by non-lead paint. The measurement yields the total mass of lead in the target area; that is, the mass per unit area of lead. Another embodiment of this invention is the measurement of a target element that is approximately uniformly distributed throughout a substrate that is thick compared to the range of the photons being detected. An example of this embodiment is the detection of lead in the bone of living people; the lead-bearing bone is generally several centimeters thick while the penetration depth of the L x-rays is only millimeters thick. The bone is covered by fat, muscle and skin of varying thicknesses depending on the subject being tested. The present invention allows one to measure the concentration of the lead in the bone without knowing either the thickness or the composition of the tissues covering the bone. The measurement gives the concentration in mass (grams) of the target element (for example, lead), per mass (grams) of the matrix or substrate (for example, bone); that is, it gives the mass fraction of the target element in its matrix.

DESCRIPTION OF PREFERRED EMBODIMENT

Figure 1:
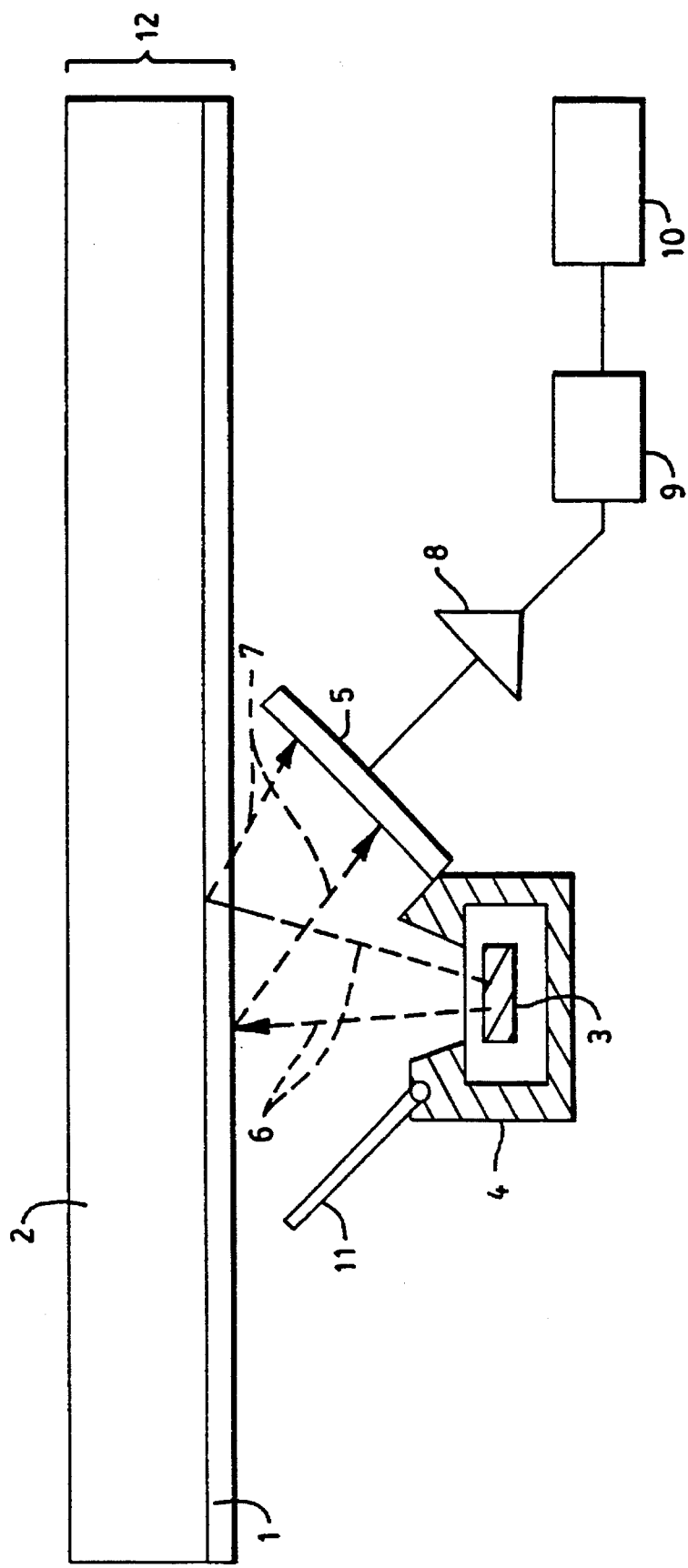
FIG. 1. A schematic of the principal elements in the invention, including a source of initiating radiation 3, a safety cover on the source 11, a sample 12 consisting of its surface I on a substratum 2, and a detector 5 that measures the back-detected radiations 7.

The intensity $I_L(\alpha,\beta)$ of each of the L x-ray lines from a lead concentration $m_{lead}$ in mg/cm², is given by Equation 1a and 1b.

$$I_L(\alpha)=I_oP(\alpha)\Omega_{inc}a_{inc}m_{lead}a_{out}(\alpha)\Omega_{det}\epsilon(\alpha) \qquad 1a)$$

$$I_L(\beta)=I_oP(\beta)\Omega_{inc}a_{inc}m_{lead}a_{out}(\beta)\Omega_{det}\epsilon(\beta). \qquad 1b)$$

$I_o$ is the intensity per steradian of the initiating photons (such as the 22.1 keV x-rays from $^{109}$Cd), $P(\alpha,\beta)$ are the probabilities of the initiating photon to produce an $L_\alpha$ or $L_\beta$ x-ray, respectively, in 1 mg/cm² of lead, $\Omega_{inc}$ is the solid angle of the irradiated sample with respect to the radiation source, $\Omega_{det}$ is the solid angle of the detector with respect to the source of lead x-rays, $a_{inc}$ is the attenuation of the initiating photons (e.g. 22.1 keV) on passing through the material to the lead layer, $a_{out}(\alpha,\beta)$ are the attenuations of the $L_\alpha$ and $L_\beta$, respectively, of x-rays exiting from the lead layer, and $\epsilon(\alpha,\beta)$ are the efficiencies of the detector to detect the $L_\alpha$ and $L_\beta$ x-rays, respectively.

The probability, $P(\alpha)$ and $P(\beta)$ that a 22.1 keV photon (from $^{109}$Cd) will induce an $L_\alpha$ or an $L_\beta$ x-ray, respectively, from a layer of lead 1 mg/cm² thick is about 1%. The yield of L x-rays increases linearly with the thickness of lead until self-attenuation becomes appreciable at about 5 mg/cm². The total L x-ray yield reaches an asymptotic limit of about 10% at a lead thickness of about 15 mg/cm².

The areal density of the target element, e.g. lead, is given by rearranging Equations 1a and 1b.

$$m_{lead} = \frac{I_L(\alpha)}{I_o P(\alpha) \Omega_{inc} a_{inc} a_{out}(\alpha) \Omega_{det} \epsilon(\alpha)} \quad \text{2a)}$$

$$m_{lead} = \frac{I_L(\beta)}{I_o P(\beta) \Omega_{inc} a_{inc} a_{out}(\beta) \Omega_{det} \epsilon(\beta)} \quad \text{2b)}$$

One measures two quantities $I_L(\alpha)$ and $I_L(\beta)$. The products of the fixed or geometrical parameters, $[I_o\, P(\alpha,\beta)\, \Omega_{inc}\, \Omega_{det}\, \epsilon(\alpha,\beta)]$, for the $L_\alpha$ and $L_\beta$ x-rays, respectively, can be accurately determined by measuring, in the same geometry that is used for measuring the unknown, the intensities of the $I_L(\alpha)$ and $I_L(\beta)$ x-rays induced from a "standard lead sample", consisting of a surface layer of lead of known areal thickness on a known substrate. Equations 2a and 2b still contain, however, four unknowns: $m_{lead}$, $a_{inc}$, $a_{out}(\alpha)$ and $a_{out}(\beta)$. Until now, there has only been two situations when the analysis for $m_{lead}$ could be made without extra assumptions or ambiguities. First, when the lead is at or close to the surface, so that $a_{inc} \approx a_{out} \approx 1$ and $m_{lead}$ is determined directly by the measurement of either $I_{L_\alpha}$ or $I_{L_\beta}$. Second, when the nature of the covering material is known, so that the mass attenuation coefficients are also known. In that case, Equations 2a and 2b have but two unknowns, $m_{lead}$ and the thickness of the covering layer, and the measurements of $I_L(\alpha)$ and $I_L(\beta)$ are sufficient to determine both. In the general case, however, of an unknown material of unknown thickness, Equations 2a and 2b cannot yield $m_{lead}$. We will show, however, that there is additional information not previously considered that makes it possible to determine $m_{lead}$ even when covered by layers of unknown material of unknown thickness. We begin by examining lead on the surface of a substrate, uncovered by material that significantly attenuates the signals.

Figure 2:
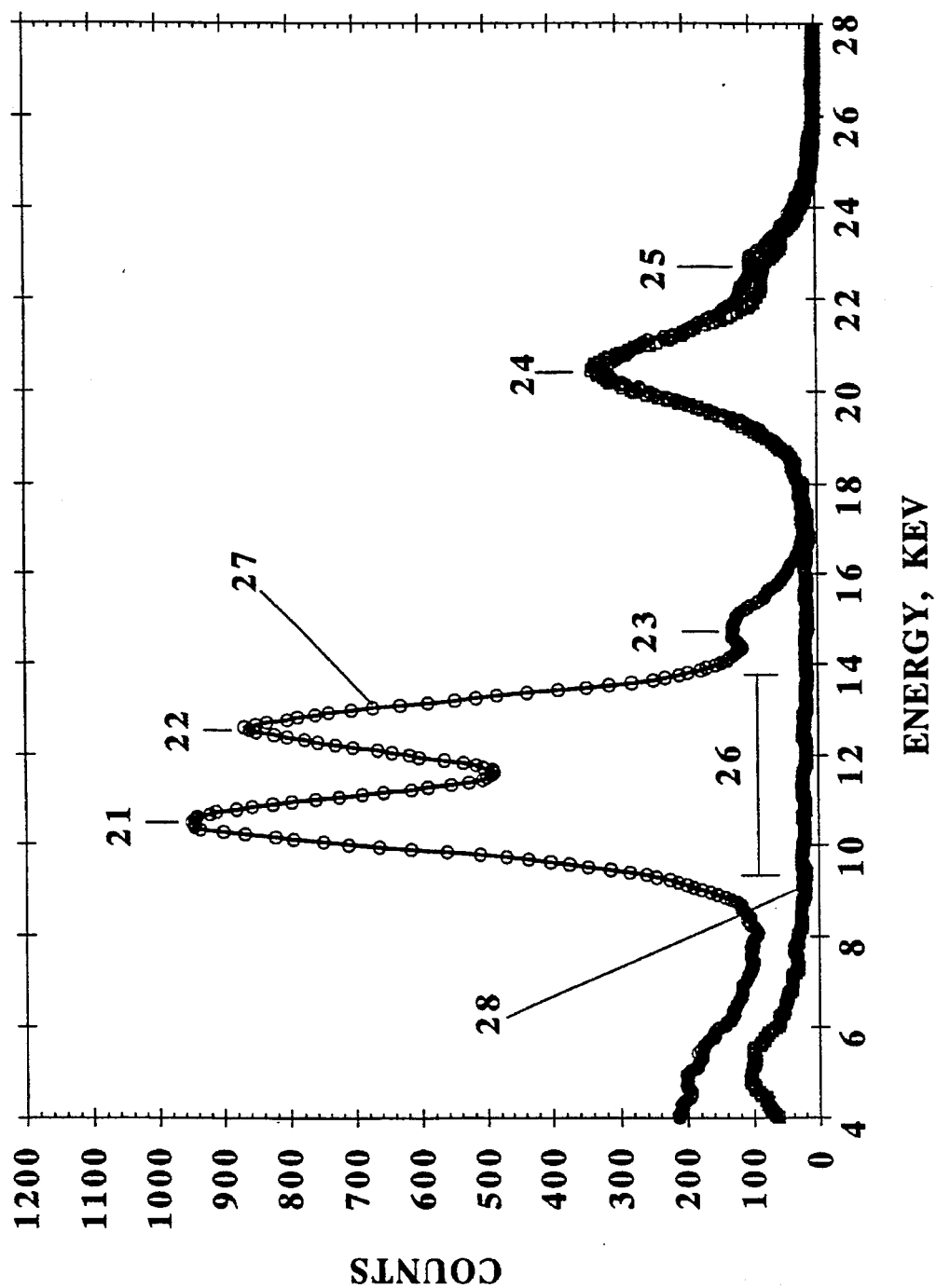
FIG. 2. A spectrum 27 of the intensity of the photons versus the energy of the photons obtained with a $^{109}$Cd source, a PIN silicon diode and a target of wood with a surface layer of 1.6 mg/cm² of Pb in the form of lead paint. A spectrum 28 of the wood without the lead paint is also shown for comparison; the two spectra were normalized at the Compton peak to show the true background under the L lines of spectrum 27. The geometry was similar to that of FIG. 1. The $L_\alpha$ x-rays 21, $L_\beta$ x-rays 22 and $L_\gamma$ x-rays 23 are induced in the lead paint layer 1, while the Compton scattered peaks 24 and 25 arise from scattering of the initiating radiation in the sample 1 and substratum 2.

FIG. 2 shows an actual spectra obtained from 1.6 mg/cm² of surface lead in a geometry similar to, though not as efficient as, FIG. 1. The target was a "standard" supplied by the Massachusetts Department of Health that consisted of a board of wood, half of one face being painted with non-lead and the other half being painted with paint containing 1.6 mg/cm² lead. The initiating source was 0.7 mC of $^{109}$Cd, the detector was a PIN silicon diode, with an area of 0.1 cm² and a thickness of ~200 µm. The net count rate of $L_\alpha$ and $L_\beta$ x-rays in FIG. 2 were 320 and 280 counts per second respectively with a background 26 of 18 counts per second. A paint layer containing only 1 mg/cm² would have yielded about 200 counts per second in each of the L peaks. In 0.1 second, we obtain 20 counts per second in each peak, with a background of 3 counts per second. Thus, using a relatively weak source of initiating radiation, and with a detector that has an area that is 10 to 30 times smaller than commercially available, we have shown that the presence of 1 mg/cm² of surface lead can be determined in a tenth of a second with a confidence level exceeding 95% (3 standard deviations). These results are at least two orders of magnitude better than from any XRF lead-paint detector on the market now.

The effectiveness of an LXF system will not be much diminished if the lead is covered by only a few layers of non-lead paint below the surface. And it will be appreciated that if stronger sources and more efficient geometries are used, (typical XRF lead detectors use source strengths of at least 10 mC), the LXF method should be able to detect 0.005 mg/cm² of surface lead, that is 5 parts per million in a 10 second measurement. LXF is at least two orders of magnitude more sensitive for detecting lead on or near the surface than the present standard of 1 mg/cm² and more than one order of magnitude more sensitive than the most sensitive of the present XRF field instruments based on K x-ray counting.

When the lead is covered with layers of non-lead paint, we must account for $a_{inc}$, $a_{out}(\alpha)$ and $a_{out}(\beta)$, the attenuations of the initiating photons through the cover layers into the lead layer and the attenuation of the L x-rays out through the same thickness of cover layers. Prior to this invention there has been no method to do that without knowing the nature of the covering material.

The principal new idea underlying this invention is the realization that the ratio of the mass attenuation coefficient for the $L_\alpha$ x-rays to that of the $L_\beta$ x-rays is independent of atomic number, and that the ratio of the mass attenuation coefficient for $L_\beta$ (or $L_\alpha$) x-rays to that of 22.1 keV x-rays is also effectively independent of the atomic number of the covering layer. The constancy of these ratios are exploited to measure the absolute value of the lead concentration under many layers of non-lead paint, without knowing either the thickness of the covering layer or the material of which it is made. The analytic procedure to obtain the concentration of lead using this new idea is as follows:

Equations 1a and 1b are recast in terms of the intensities of the $L_\alpha$ and $L_\beta$ x-rays at their point of origin in the lead layer, $I^o(\alpha)$ and $I^o(\beta)$ $$I_L(\alpha) = I^o(\alpha) a_{out}(\alpha) \Omega_{det} \epsilon(\beta). \quad \text{3a)}$$

$$I_L(\beta) = I^o(\beta) a_{out}(\beta) \Omega_{det} \epsilon(\beta). \quad \text{3b)}$$

where $$I^o(\alpha) = I_o P(\alpha) \Omega_{inc} a_{inc} m_{lead} \quad \text{4a)}$$

$$I^o(\beta) = I_o P(\beta) \Omega_{inc} a_{inc} m_{lead} \quad \text{4b)}$$

The attenuation factors $a(\alpha)$ and $a(\beta)$ (dropping the qualifier "out") are explicitly, $$a(\alpha) = e^{-\mu(\alpha)t/\cos\theta} \quad \text{5a)}$$

$$a(\beta) = e^{-\mu(\beta)t/\cos\theta} \quad \text{5b)}$$

$$a_{inc} = e^{-\mu(inc)t/\cos\omega} \quad \text{5c)}$$

where $\mu(\alpha)$, $\mu(\beta)$ and $\mu(inc)$ are the mass attenuation coefficients, in cm²/g, of the cover material for the $L_\alpha$ x-rays, $L_\beta$ x-rays and the incident initiating photons respectively, t is the thickness of the covering layer in g/cm², and $\theta$ and $\omega$ are the angles with respect to the perpendicular to the thickness made by the fluorescent and incident radiation respectively.

Taking the natural logarithms of both sides of Equations 5 we obtain Equations 6.

$$\ln a(\alpha) = -\mu(\alpha)t/\cos\theta \quad \text{6a)}$$

$$\ln a(\beta) = -\mu(\beta)t/\cos\theta \quad \text{6b)}$$

$$\ln a_{inc} = -\mu(inc)t/\cos\omega \quad \text{6c)}$$

Form the ratios of Equation 6a to Equation 6b.

$$\frac{\ln a(\alpha)}{\ln b(\beta)} = \frac{\mu_\alpha}{\mu_\beta} = R_1 \quad \text{6)}$$

Form the ratio of Equation 6c to Equation 6b.

$$\frac{\ln a_{inc}}{\ln a(\beta)} = \frac{\mu_{inc}\cos\theta}{\mu_\beta\cos\omega} = R_2 \qquad 7)$$

For simplicity in the arguments that follow we will ignore the dependence of $R_2$ on deviations from the normal of the angles of incidence and emission, noting only that for most applications the angular contribution is small, though it should be included for the most precise analysis.

The surprising fact that we have discovered is that, for all practical purposes, $R_1$ and $R_2$ (for a fixed geometry) are constants for all materials for the photon energies of interest to this patent. In particular, $R_1$ is a constant, to within 5%, for the $L_\alpha$ and $L_\beta$ x-rays of all heavy elements. The constancy of $R_1$ and $R_2$ is the cornerstone of this invention since it provides two further equations that make it possible to eliminate the unknown attenuation coefficients from Equations 2 and solve for the unknown mass in terms of the intensities of the $L_\alpha$ and $L_\beta$ x-rays only. Before taking up the explicit equations we consider the constancy of $R_1$ and $R_2$ for the measurement of lead using the 22.1 keV radiation of $^{109}$Cd.

The mass attenuation coefficients, in cm²/g, for various materials are listed in the upper part of Table 1 for x-ray energies relevant to the measurement of lead using $^{109}$Cd: 10.5 keV, 12.6 keV, 15 keV and 22.1 keV. The values, apart from TiO$_2$ and ZnO, were obtained from *Photon Cross Sections, Attenuation Coefficients, and Energy Absorption Coefficients from 10 keV to 100 GeV*, NSRDS-NBS 29, 1969. The values for TiO$_2$ and ZnO were calculated from the values for the constituent elements.

for the L lines of lead. The second row of Table 1b gives the ratio $R_2$ for the L($\beta$) line of lead and the 22.1 keV photons of $^{109}$Cd. The central point of this table is that all of the $R_1$ values of practical interest fall between 1.64 and 1.72; i.e. $R_1=1.68\pm0.05$. The $R_1$ values are the same within 2.5% of the mean. (The ratio varies by only 4% if we include materials as heavy as uranium.) The values of $R_2$ have a greater variation but, apart from the lightest absorbers, are also constant. For the purposes of this invention, the ratio of mass attenuation coefficients $R_1$ and $R_2$ are independent of the material covering the lead.

The constancy of $R_1$ is unexpected. In fact, the variation of the ratio of mass attenuation coefficients with atomic number is widely used in so-called "dual-energy x-ray analysis" to determine the atomic number of the absorber. The bottom row of Table 1b demonstrates this variation by comparing 10 keV photons with 30 keV photons; the ratio of the $\mu$ values varies by 250% on going from lucite to calcium. (The sharp drop in the ratio at tin is due to the critical absorption of the K shell electrons.) The constancy of the ratio for the special case of the $L_\alpha$ and $L_\beta$ x-rays has never before been utilized.

We now proceed to show how the constancy of $R_1$ and $R_2$ allows the measurement of the absolute concentration of lead, independent of the thickness and nature of the material covering the lead. We write Equations 1 explicitly $$I_L(\alpha)=I_oP(\alpha)\Omega_{inc}e^{-\mu_{inc}t}m_{lead}e^{-\mu(\alpha)t}\Omega_{det}\epsilon(\alpha). \qquad 8a)$$

$$I_L(\beta)=I_oP(\beta)\Omega_{inc}e^{-\mu_{inc}t}m_{lead}e^{-\mu(\beta)t}\Omega_{det}\epsilon(\beta). \qquad 8b)$$

Equations 6 and 7 are used to eliminate ($\mu_{inc}t$) and ($\mu_\alpha t$) from

TABLE I

Mass attenuation Coefficients for X-rays from 10 key to 30 key, in cm²/g.

|  | Lucite | Al | TiO$_2$ | Ca | Fe | Cu | ZnO | Sn |
|---|---|---|---|---|---|---|---|---|
| Energy keV |  |  |  |  |  |  |  |  |
| 10.0 | 3.3 | 26.6 | 66.2 | 96.5 | 173 | 224 | 190 | 141 |
| 10.5 | 2.8 | 23 | 57.7 | 83.9 | 151 | 196 | 166 | 123 |
| 12.6 | 1.7 | 13.3 | 34.5 | 49.7 | 91 | 119 | 101 | 75.4 |
| 15.0 | 1.1 | 7.9 | 21.1 | 30.1 | 56 | 74 | 63 | 47 |
| 20.0 | 0.6 | 3.4 | 9.4 | 13 | 26 | 34 | 29 | 21 |
| 22.1 | 0.5 | 2.6 | 7.1 | 9.7 | 19.2 | 25.4 | 22 | 16 |
| 30.0 | 0.3 | 1.1 | 3.0 | 4 | 8 | 11 | 9.66 | 41 |
| Ratio, R |  |  |  |  |  |  |  |  |
| $R_1 = \mu(10.5)/\mu(12.6)$ | 1.65 | 1.72 | 1.67 | 1.69 | 1.66 | 1.64 | 1.64 | 1.64 |
| $R_2 = \mu(22.1)/\mu(12.6)$ | 0.28 | 0.2 | 0.2 | 0.2 | 0.21 | 0.21 | 0.21 | 0.21 |
| $R_3 = \mu(12.6)/\mu(15)$ | 1.55 | 2.91 | 2.73 | 2.79 | 2.70 | 2.65 | 2.63 | 2.62 |
| $\mu(10)/\mu(30)$ | 10.9 | 23.5 | 22.1 | 24.1 | 21.6 | 20.0 | 19.7 | 3.4 |

The mass attenuation coefficients for x-rays from 10 keV to 30 keV vary strongly both as a function of the materials and as a function of energy. For a given material, the attenuation coefficients for the 10.5 keV x-ray is greater than that for the 12.6 keV x-ray which, in turn is considerably greater than that for the 22.1 keV x-ray. The variation with atomic number is even more dramatic: the attenuation coefficients for the 10.5 keV $L_\alpha$ line of lead varies by more than a factor of 70 on going from lucite (average atomic number ~6.5) to copper (atomic number 29); that is, the thickness of lucite (in cm²/g) must be 70 times that of copper to attenuate the $L_\alpha$ lines of lead by the same amount.

The ratios of the attenuation coefficients are given in Table 1b, the lower part of Table I, for materials spanning lucite (such as an lucite-based paint) to tin (atomic number 50). The first row (bold type) of Table 1b gives the ratio $R_1$ Equations 8a and 8b. The results are:

$$I_L(\alpha)=I_oP(\alpha)\Omega_{inc}e^{R_2\ln a(\beta)}m_{lead}e^{R_1\ln a(\beta)}\Omega_{det}\epsilon(\alpha). \qquad 9)$$

$$I_L(\beta)=I_oP(\beta)\Omega_{inc}e^{r_2\ln a(\beta)}m_{lead}a(\beta)\Omega_{det}\epsilon(\beta). \qquad 10)$$

Equations 9 and 10 contain two unknowns, the mass of the lead and $a(\beta)$ the attenuation of the $L_\beta$ x-rays out from the lead layer. (It will be appreciated that we could have cast Equations 9 and 10 in terms of the unknown mass and any of the three attenuation factors, $a(\alpha)$, $a(\beta)$ or $a(inc)$.)

Eliminating $a(\beta)$ from Equations 9 and 10, yields, after some algebraic manipulations, the desired result of the areal density of the unknown in terms of the measured intensities of the $L_\alpha$ and $L_\beta$ x-rays and known parameters of the detector and the geometry. Eliminating $m_{lead}$ from Equations 9 and 10, yields the absorption of the covering layer in terms of the same measured quantities. We consider this point explicitly below. The result, Equation 11, is for the areal density of any element, Z, under study by measuring the intensity of the $L_\alpha$ and $L_\beta$ x-rays.

$$m_Z = \left[ \frac{I_L(\beta)}{I_o \Omega_{inc} \Omega_{det} P(\beta) \epsilon(\beta)} \right]^{(R_1+R_2)/(R_1-1)} \left[ \frac{I_o \Omega_{inc} \Omega_{det} P(\alpha) \epsilon(\alpha)}{I_L(\alpha)} \right]^{(R_2+1)/(R_1-1)} \quad 11)$$

$R_1$ is the ratio of attenuation coefficients for the $L_\alpha$ to $L_\beta$ x-rays of the element Z being studied and $R_2$ is the ratio of the attenuation coefficients for the initiating radiation to the $L_\beta$ radiation. Without loss of generality we could use the $L_\alpha$ radiation for comparison with the initiating radiation. Without loss of generality we could use the $L_\beta$ and $L_\gamma$ x-rays of the target element to deduce the mass of the target element.

Equation 11 is quite remarkable. By measuring the intensity of the $L_\alpha$ and $L_\beta$ x-rays with a known source strength and geometry, we can obtain the absolute measurement of the concentration of an element such as lead even when the element is covered by many layers of unknown thickness and composition.

Equation 11 is independent of the material or thickness of the layers covering the target element. It therefore applies to the measurement of a standard sample which has no covering layer. This fact allows us to obtain the products $I_o \Omega_{inc} \Omega_{det} P(\alpha,\beta) \epsilon(\alpha,\beta)$ using a standard sample of the same element as the target, placed in the target geometry. The areal density of the unknown target element is then given with respect to the areal density of the known standard by measuring the intensities of the $L_\alpha$ and $L_\beta$ x-rays from the unknown in terms of the intensities $L_\alpha$ and $L_\beta$ x-rays from the known standard of areal mass, $m_{standard}$, and substituting these measured intensities into Equation 12.

$$m_Z = m_{standard} \frac{I_{L_\beta}^{(R_1+R_2)/(R_1-1)} / I_{L_\alpha}^{(R_2+1)/(R_1-1)}}{[I_{L_\beta}^{(R_1+R_2)/(R_1-1)} / I_{L_\alpha}^{(R_2+1)/(R_1-1)}]_{standard}} \quad 12)$$

In the further discussions of this invention we will assume analytic forms such as Equation 12 that include the use of a standard. We emphasize, however, that the master equation is Equation 11 and that the fixed factors $I_o \Omega_{inc} \Omega_{det} P(\alpha,\beta) \epsilon(\alpha,\beta)$ can be obtained by other means than the use of standards, though we expect that the use of standards is the most practical way of determining those factors.

For the study of lead using the 22.1 keV radiation of $^{109}$Cd, the values of $R_1$ and $R_2$ are given in Table 1b: $R_1 = 1.68$ and $R_2 \approx 0.20$. Equation 12, becomes simply, $$m_{lead} = m_{stand} \frac{I_{L_\beta}^{2.76} / I_{L_\alpha}^{1.76}}{[I_{L_\beta}^{2.76} / I_{L_\alpha}^{1.76}]_{stand}} = \quad 13)$$

$$m_{stand} \left[ \frac{I_{L_\beta}/I_{L_\alpha}}{[I_{L_\beta}/I_{L_\alpha}]_{stand}} \right]^{1.6} \frac{I_{L_\beta}}{[I_{L_\beta}]_{stand}}$$

We have not used the intensity of the $L_\gamma$ x-rays in the above analysis. The $L_\gamma$ x-rays will become important when the covering layer has an absorptive thickness for the $L_\alpha$ x-rays of about 2 mean free paths. In that event, the analysis could proceed using the $L_\beta$ and $L_\gamma$ x-rays since, as shown in Table 1, the ratio of the mass absorption coefficients for $L_\beta$ and $L_\gamma$ rays of lead is also independent of the covering material, apart from very light covering materials such as lucite which have very little absorptive power. Equations 11, 12 and 13 are then modified appropriately.

A few comments about LXF:

The LXF method also yields the attenuation suffered by the x-rays. That is, it allows the determination of the product of the mass attenuation factor times the thickness of the covering layer. The method does not, by itself, give information of either the nature or the thickness of the covering material separately. Nevertheless, as we emphasize below, the absorption by the covering layer is a good index of the depth of the lead paint below the surface.

The LXF method requires that the intensities of at least two of L x-ray lines, i.e. the $L_\alpha$ and $L_\beta$, $L_\alpha$ and $L_\gamma$, or $L_\beta$ and $L_\gamma$, be measured. Since the energy difference between the L lines is proportional to the square of the atomic number, the practicality of the method depends on the energy resolution of the available detectors. The LXF method is especially appropriate for field measurements of lead and elements such as mercury, gold and uranium since inexpensive detectors are available with energy resolutions that can separate the L spectra, as exampled in FIGS. 2, 3, 4 and 5.

As the LXF method is applied to lighter and lighter elements, the ratio $R_1$ of the mass attenuation factors for the $L_\alpha$ and $L_\beta$ (or $L_\beta$ and $L_\gamma$) x-rays approaches 1, the denominator factor $(R_1-1)$ approaches zero and the exponential terms go towards infinity. The LXF method appears to be quite practical for elements as light as the rare earths, where $(R_1-1) \approx 0.3$, but may not be appropriate for much lighter elements.

The attenuation factors for light covering material such as lucite paint are almost always small since the mean free path even for the 10.5 keV x-ray is almost 4 mm. The detector will analyze the paint as if the lead were on the surface. Thus, for all practical purposes we can ignore the anomalously high values of $R_2$ for lucite and other light-element paints and set $R_2 = 0.2$ in Equation 10.

The attenuation of the excitation radiation that occurs in the covering layers decreases rapidly as the energy of the incident photon increases. If the excitation energy is sufficiently high, the attenuation can be neglected. For example, if the lead in paint is excited by the 43 keV $K_\alpha$ x-rays of $^{157}$Gd (from the 150 year source of $^{157}$Tb), then the 43 keV radiation will suffer negligible absorption in the covering layers of paint. In that case, $R_2$ can be omitted from the above formulas, and Equation 12 simplifies to Equation 14, $$m_Z = m_{stand} \frac{I_{L_\beta}^{R_1/(R_1-1)} / I_{L_\alpha}^{1/(R_1-1)}}{[I_{L_\beta}^{R_1/(R_1-1)} / I_{L_\alpha}^{1/(R_1-1)}]_{standard}} \quad 14)$$

Standards for lead paint, that is, sheets of paint containing known amounts of lead in the range from 0.3 mg/cm$^2$ to 4 mg/cm$^2$, can now be obtained from the National Institutes for Standards and Technology.

To illustrate the LXF technique we show the results in FIGS. 2, 3, 4 and 5. obtained with our preferred embodiment. The lead paint standard, supplied by the Massachusetts Department of Public Health, was a piece of wood half of which was covered with 1 mg/cm² of lead paint, the other half was painted with non-lead paint. The source was 0.7 mC $^{109}$Cd source, so $I_o=2\times10^6$/steradian/second. The detector was a silicon PIN diode, with an area of 0.1 cm² and a thickness of about 200 μm, such as the Hammamatsu S 1223-01. The energy resolution for this detector was about 1.5 keV. The efficiencies of this diode for detecting the 10.5 keV and 12.6 keV radiations were ~0.7 and ~0.5 respectively so that the measured intensity of the I(10.5 keV) was approximately equal to the intensity of the I(12.6 keV) line. The geometrical factors in Equation 1 were: $\Omega_{inc}=\Omega_{det}\approx0.6$ steradians. The count rates in each of the L peaks were ~250/sec. With a coveting layer, the incident 22.1 keV radiation will be absorbed on the way into the lead layer, and the 10.5 keV and 12.6 keV x-rays will be absorbed on the way out to the detector. The attenuations are governed by the mass absorption coefficients. For illustrative purposes we consider TiO₂, since it will be appreciated that TiO₂ paints are probably the most commonly used and the method does not depend on the choice of covering material. The mass attenuation coefficients in pure TiO₂ for 10.5 keV, 12.6 keV and 22.1 keV, are, from Table 1, 58 cm²/g, 34.5 cm²/g and 7.1 cm²/g, respectively. A single layer of the TiO₂ paint had a total equivalent thickness of 6 to 10 mg/cm² of TiO₂, depending on the brand and how the paint was laid down.

Figure 3:
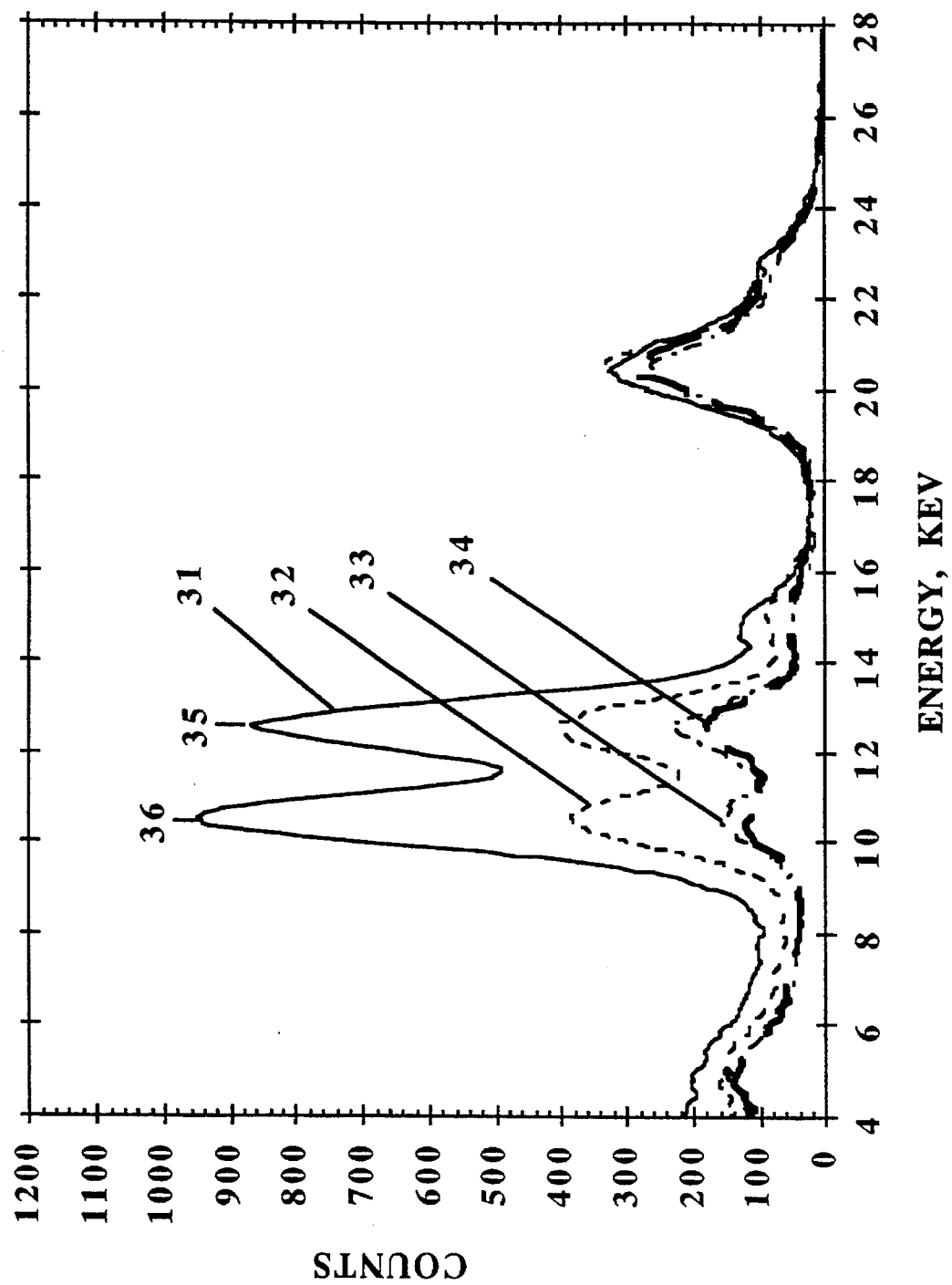
FIG. 3. Spectra taken with the same geometry as that of FIG. 2 showing the effects of covering layers of $TiO_2$ on the spectrum 31 obtained from a 1.6 mg/cm² Pb paint on wood standard. Spectra 32, 33 and 34 were obtained with covers of 2, 4 and 6 layers of $TiO_2$ paint respectively. The lead $L_\alpha$ 36 diminishes more rapidly than the $L_\beta$ 35 peak as the thickness increases, but is still easily visible through 6 layers of paint.

FIG. 3 shows the effect of coveting the lead paint on wood 31 with 2 layers 32, 4 layers 33 and 6 layers 34 of TiO₂ paint. The total areal density of the last sample was ~100 mg/cm², of which more than half was TiO₂. The $L_\alpha$ 36 and $L_\beta$ 35 lines continue to be readily observable, with net count rates of more than 18 counts per seconds versus a background of 14 counts per second. A 1 second test would yield the unambiguous presence of lead concentration (3 standard deviations). The absolute amount of lead would be obtained to an uncertainty of about 25% in a 10 second test.

Figure 4:
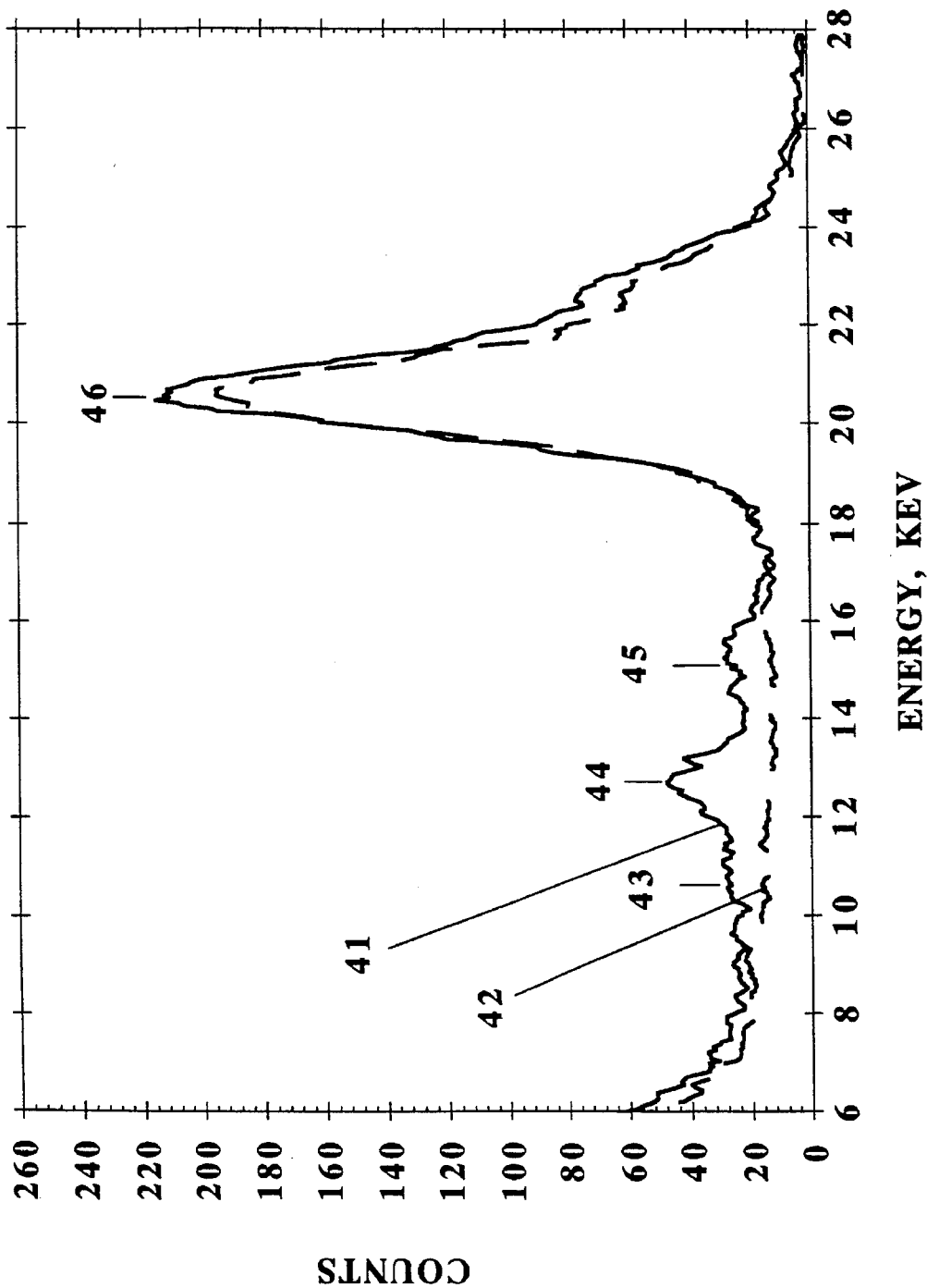
FIG. 4. Spectra taken with the same geometry as that of FIG. 2 comparing the spectrum 42 obtained with ten layers of $TiO_2$ paint on wood with the spectrum 41 obtained with the same ten layers of $TiO_2$ paint on 1.6 mg/cm² of lead paint on the same wood. The $L_\alpha$ peak of lead 43 is almost gone, but the $L_\beta$ 44 and $L_\gamma$ 45 peaks continue to be readily measured above the background due to the Compton peaks 46.

FIG. 4 compares the spectrum of 1.6 mg/cm² of lead paint covered with ten layers of TiO₂ paint 41 with the spectrum of the same ten layers on wood alone 42. This figure illustrates the use of the $L_\beta$ 44 and $L_\gamma$ 45 lines to determine the lead concentration when the $L_\alpha$ 43 line is too strongly absorbed to be quantitatively measured. The intensity of the L x-rays has dropped to 10 counts per second, with a background of 15 counts per second. A one second measurement gives a two standard deviation indication of the presence of lead, a one minute reading yields the lead concentration.

OTHER FEATURES OF THE BACK-DETECTED SPECTRUM

The Compton scattered peak 23 of FIG. 2 is a ubiquitous component of the back-detected spectrum when the initiating radiation is a mono-energetic or nearly mono-energetic photon beam. The spectrum of the back-detected Compton radiation consists of a single peak at the Compton energy and a long, low-energy tail extending to zero energy. That tail originates in the detector and not in the sample. The ratio of the intensity of the low-energy tail, which constitutes the background under the L x-rays of the lead, to the intensity of the Compton peak, is a constant for a given detector. Thus, the background under the L x-rays can be quantitatively and accurately determined by measuring the intensity of the Compton peak 46.

Figure 5:
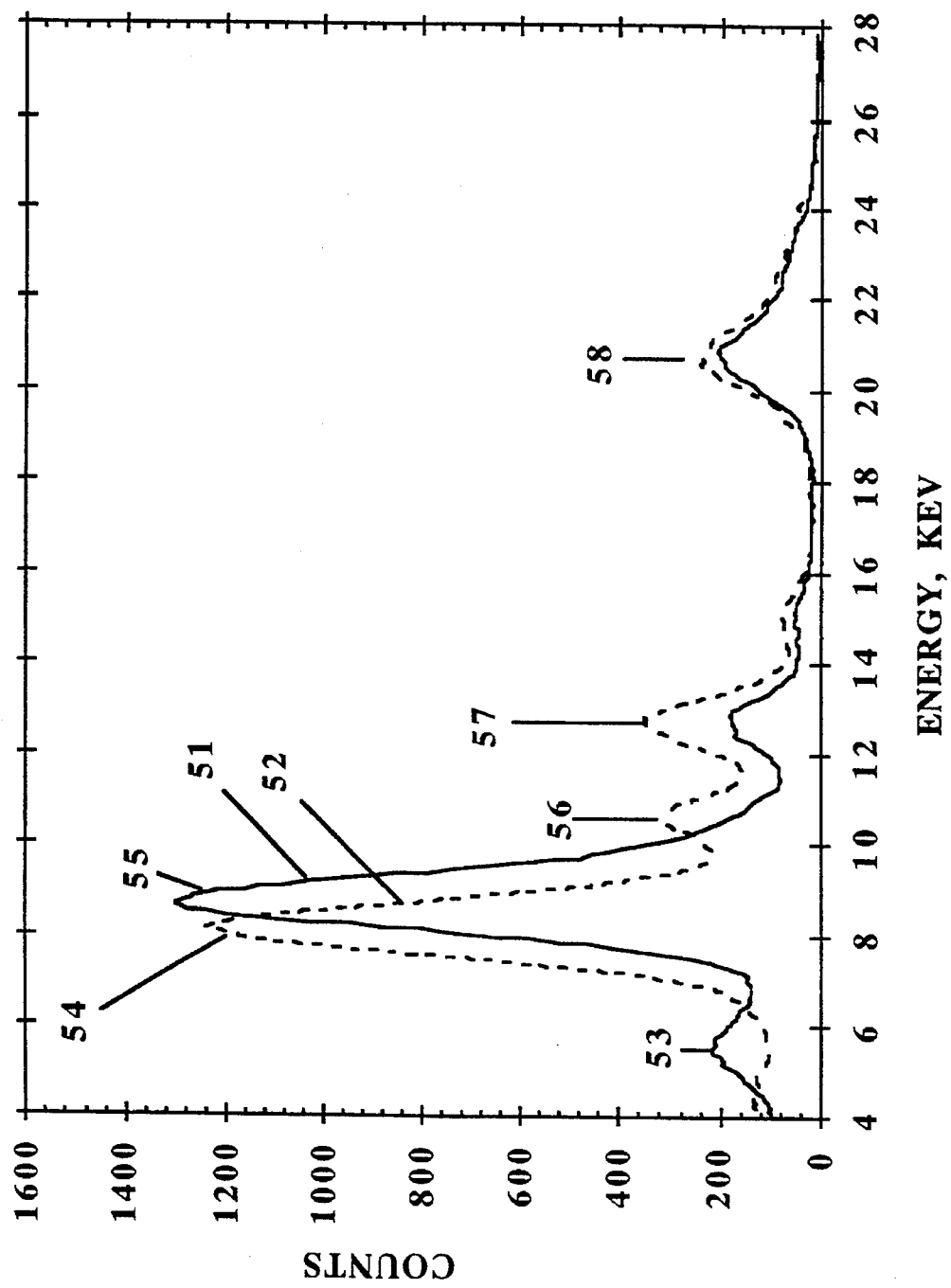
FIG. 5. Spectra taken with the same geometry as that of FIG. 2. Spectrum 51 was obtained with the 1.6 mg/cm² lead paint standard covered with zinc-chromate based paint. Spectrum 52 was obtained with the cover layer changed to a copper-based paint.

Some non-lead paints so strongly absorb the lead L x-rays that relatively few overlayers are needed to mask the lead signal. ZnO is such a paint, CuO is another. Table 1 shows that the mass attenuation coefficients for ZnO are about 3 times that of TiO₂ so that it takes only about 30 mg/cm² (3 to 4 layers) of ZnO cover to effectively camouflage the lead. However, zinc or copper based paints are self-incriminating. If either is present, it will makes itself known by emitting an easily identified fluorescent x-ray. That is, the very absorption by the zinc reveals its presence since the absorption is dominantly by the photoelectric effect, which results in the emission of the zinc $K_\alpha$ x-rays at 8.6 keV. This important advantage of the LXF method is illustrated in FIG. 5, which shows the spectra, obtained in the geometry used to obtain the spectra of FIGS. 2, 3 and 4, for 1.6 mg/cm² of lead paint on wood, covered by a single layer of zinc chromate paint 51 and by a single layer of a copper-based paint 52. In both cases, the peaks from the metals completely dominate the spectra, though the lead lines are still easily observed. Tests of one second duration easily reveal the presence of even small quantities of these metal paints. The intensities of the peaks, such as 54 for copper, and 55 for zinc and 53 for the chromate, give measure to the thickness of the paint layers and those thicknesses can be used to determine whether sufficient metal is on the substrate to completely obscure the presence of underlying lead. If that is the case, the LXF detector would give a null reading indicating that a conclusion cannot be drawn as to the presence of lead.

OTHER EMBODIMENTS

The LXF invention has been illustrated with the use of the 22.1 keV x-ray from $^{109}$Cd source, which is an appropriate source for measuring the concentrations of all heavy elements, including uranium. $^{109}$Cd is especially appropriate for lead since the 22.1 keV x-ray is sufficiently close to the 13 to 16 keV binding energies of the L electrons of lead to photo-excite the atoms strongly, yet is far enough removed from the energy of the lead L x-rays that the incoherent (Compton) scattering of the 22.1 keV photons do not interfere with the measurements of those x-rays. We note, however, that other sources of initiating radiation can be used that emit photons with an energy greater than the 13.035 keV binding energy of the L3 electrons of lead. Among the choices are $^{57}$Co with its gamma ray at 14.4 keV, $^{241}$Am with its gamma ray of 59.5 keV and strong L x-rays at 13.9 keV and 17.8 keV, $^{157}$Tb, with a half life of 150 years and a strong $K_\alpha$ x-ray at 43 keV, and portable x-ray tubes that generate K x-rays greater than 13.035 keV.

The LXF invention has been illustrated with the use of a silicon PIN diode detector, which is relatively inexpensive and can be obtained from a number of manufacturers. FIGS. 2, 3, 4 and 5 show that the detector, operating at room temperature, can have an energy resolution of about 1.5 keV in the energy range of interest and satisfies the requirement of being able to resolve the $L_\alpha$, $L_\beta$ and $L_\gamma$ x-rays of lead. We note that there are other choices for detectors that have comparable or superior energy resolutions and efficiencies, among them being proportional counters, avalanche photodiodes, cooled lithium-drifted silicon detectors, cooled germanium detectors, and inorganic scintillators.

An important embodiment of this invention is its use in measuring lead in the bone of people, in particular children. This is an important application of x-ray fluorescence. U.S. Pat. No. 4,845,729, to Rosen et al discloses that the L x-rays of lead can be used for the in situ measurement of lead in the tibia. Rosen excites the L x-rays by an x-ray generator of special design. The L x-rays of lead from the bone are attenuated by the layers of covering tissue consisting primarily of fat and skin. Rosen must correct for that attenuation, especially when the fat layer exceeds a few millimeters. Rosen et al suggest that the correction be made on the basis of the thickness measured by an ultrasonic technique. He also suggests that the lead concentration can be deduced by comparing the x-ray fluorescent spectrum obtained from a subject with a catalogue of spectra from subjects with known lead concentration. Both methods have large uncertainties. The present invention makes the determination of the lead concentration independent of the thickness or composition of the coveting layer. The only change in equations 12 and 14 is that the areal density, m in g/cm$^2$, must be replaced by the mass fraction, f, in grams of the target element (e.g. lead) per gram of the matrix, (e.g. bone). The general equation for $f_Z$ is, $$f_Z = f_Z(\text{stand}) \frac{I_{L_\beta}^{(R_1+R_2)/(R_1-1)} / I_{L_\alpha}^{(R_2+1)/(R_1-1)}}{[I_{L_\beta}^{(R_1+R_2)/(R_1-1)} / I_{L_\alpha}^{(R_2+1)/(R_1-1)}]_{stand}} \quad 15)$$

Equation 15 is especially applicable to measuring lead in bone. The values for $R_1$ and $R_2$, for all tissues that make up the cover layer of the tibia are remarkably constant for the L x-ray of lead excited by the 22.1 keV radiation from $^{109}$Cd: $R_1 = 1.69 \pm 0.007$; $R_2 = 0.25 \pm 0.006$. The standard for measuring lead in bone would be a piece of bone, or a phantom equivalent of bone, with a known concentration of lead.

A further embodiment of this invention is in determining the concentration of a covered element by measuring the intensities of the $K_\alpha$ and $K_\beta$ x-rays rather than the $L_\alpha$ and $L_\beta$ x-rays. The method should be especially appropriate for elements in the range from about calcium (Z=20) to about tin (Z=50) since over this range the L x-ray energies are so low that they have difficulty penetrating even the thinnest of covering layers. For calcium, the difference in energies of the $K_\alpha$ (3.69 keV) and $K_\beta$ (4.0 keV) lines is about 0.3 keV; for tin, the difference in the energies of the $K_\alpha$ (~25.2 keV) and $K_\beta$ (~28.5 keV) is about 3.2 keV. Over this entire range of elements the differences in the energies of the $K_\alpha$ and $K_\beta$ lines is small enough so that $R_1$ and $R_2$ are again essentially constant and independent of the nature of the covering layers.

The principle deterrent to using the K lines is that the intrinsic intensity of the $K_\beta$ x-ray is typically only about 10% to 20% of the intensity of the $K_\alpha$ x-ray so that an x-ray detector must have good energy resolution to measure both intensities, especially in the presence of nearby x-ray peaks. When the conditions are favorable, however, the use of the K x-rays rather than the L x-rays can be a powerful method for measuring the absolute concentration of a covered element. The relevant equations are similar to those of Equations 12 and 15. That is, if the unknown element, Z, is a thin layer covered by an unknown thickness of other elements, the areal density, $m_Z$, of the unknown is given in terms of the intensities of the K x-rays, $I_{K_\alpha}$ and $I_{K_\beta}$, of the unknown and a standard.

$$m_Z = m_{Z_{stand}} \frac{I_{K_\beta}^{(R_1+R_2)/(R_1-1)} / I_{K_\alpha}^{(R_2+1)/(R_1-1)}}{[I_{K_\beta}^{(R_1+R_2)/(R_1-1)} / I_{K_\alpha}^{(R_2+1)/(R_1-1)}]_{stand}} \quad 16)$$

The standard is an uncovered, thin layer of the target element Z of known areal density. The values of $R_1$ and $R_2$, when the method is used for K x-rays, refer to the ratios of the mass attenuation factors for K x-rays; that is, $$R_1 = \frac{\mu_{K_\alpha}}{\mu_{K_\beta}} \text{ and } R_2 = \frac{\mu_{inc}}{\mu_{K_\beta}}$$

If the incident radiation used to induce the K x-rays suffers negligible attenuation on passing through the covering layer, then the $R_2$ term can be omitted in Equation 16. The simplified equation is, $$m_Z = m_{stand} \frac{I_{K_\beta}^{1/(R_1-1)} / I_{K_\alpha}^{1/(R_1-1)}}{[I_{K_\beta}^{1/(R_1-1)} / I_{K_\alpha}^{1/(R_1-1)}]_{stand}} \quad 17)$$

If the unknown element, Z, is a component of a thick substrate that is covered by an unknown thickness of other elements, the mass fraction, $f_Z$, of the unknown is given by $$f_Z = f_{Z(stand)} \frac{I_{K_\beta}^{(R_1+R_2)/(R_1-1)} / I_{K_\alpha}^{(R_2+1)/(R_1-1)}}{[I_{K_\beta}^{(R_1+R_2)/(R_1-1)} / I_{K_\alpha}^{(R_2+1)/(R_1-1)}]_{stand}} \quad 19)$$

If the covering layer does not appreciably attenuate the radiation used to excite the K x-rays, then Equation 18 reduces to Equation 19.

$$f_Z = f_Z(\text{std}) \frac{I_{K_\beta}^{1/(R_1-1)} / I_{K_\alpha}^{1/(R_1-1)}}{[I_{K_\beta}^{1/(R_1-1)} / I_{K_\alpha}^{1/(R_1-1)}]_{standard}} \quad 19)$$

An example of the use of the K x-ray ratios is the measurement of the zinc concentration in an iron-zinc alloy that has been painted or chrome plated. By measuring the intensities of the $K_\alpha$ and $K_\beta$ lines of zinc, excited, for example, by the silver x-rays from $^{109}$Cd, one can determine the mass fraction of the zinc, in grams of zinc per gram of iron, without having to know the thickness or composition of the covering layer. In the example, the standard would be the iron alloy with a known concentration of zinc.

A further embodiment of this invention is in providing a depth index which tells whether the lead is on the surface or is buried beneath layers of non-lead paint. The ability to tell that the observed lead concentration is on the surface or is buried is a unique feature of the analytic method described herein. We are unaware of another non-destructive technique capable of making this distinction when neither the thickness nor the composition of the covering layer, nor the thickness of the primary lead layer are known.

The invention gives measure to the thickness of the non-lead paint above the leaded paint in a number of ways, all of which make use of the fact that the ratio of the intensities of the L x-rays, in particular the ratio of the intensity of $L_\beta$ to that of the $L_\alpha$ x-rays is a sensitive indicator of the absorption of the L x-rays by the cover layers. We note, without further application, that the measured intensity of the $L_\gamma$ x-ray with respect to the other two is also a measure of the depth of the lead. We describe three such measures.

First, the ratio of the intensity of the $L_\beta$ x-rays to that of the $L_\alpha$ x-rays is itself a simple measure of the depth. When the leaded paint is at or near the surface then the ratio, which depends on the energy-dependent efficiency of the detector, is typically close to one. As the thickness of the overlayer of non-lead paint increases, the ratio of the intensity of the $L_\beta$ x-rays to that of the $L_\alpha$ x-rays increases due to the preferential absorption of the $L_\alpha$ x-rays relative to the $L_\beta$ x-rays.

Second, one can obtain a precise measure of the absorption of the cover layer by determining a($\beta$) from Equations 9 and 10, by eliminating $m_{lead}$ rather than the absorption, a(b). The result, omitting angular dependent terms, is, $$\frac{1}{a(\beta)} = \left[\frac{P(\beta)\epsilon(\beta)I(L_\beta)}{P(\alpha)\epsilon(\alpha)I(L_\alpha)}\right]^{1/(R_1-1)} \quad 20)$$

When the lead layer is thin (less than a few mg/cm²) then the ratio $P(\beta)\epsilon(\beta)/P(\alpha)\epsilon(\beta)$ is the same as that of the standard. A good index, $D_{cover}$, of the thickness of the cover layer is given by the ratio normalized to the ratio observed for the standard, $$D_{cover} = \frac{1}{a(\beta)} = \left[\frac{I(L_\beta)/I(L_\alpha)}{(I(L_\beta)/I(L_\alpha))_{stand}}\right]^{1/(R_1-1)} \quad 21)$$

A very similar measure of the cover depth is given by the areal density of lead per intensity of normalized $L_\beta$ x-rays. From Equations 12 and 13, $$d_{cover} = \frac{1}{a(\beta)} \equiv \left[\frac{I(L_\beta)/I(L_\alpha)}{(I(L_\beta)/I(L_\alpha))_{stand}}\right]^{(R_2+1)/(R_1-1)} \quad 22)$$

This measure has the advantage of being obtained directly from the deduced areal density of the lead.

It should be clear that a linear measure of the depth is obtained by putting either Equation 21 or 22 in logarithmic form. Equation 21, for example, can be written $$t = \frac{1}{\mu_\beta \rho(R_1-1)} \log \frac{I(L_\beta)/I(L_\alpha)}{(I(L_\beta)/I(L_\alpha))_{stand}} \quad 23)$$

All of the parameters of Equ. 23 are measured or known except for the mass attenuation coefficient $\mu_\beta$ and the density $\rho$ of the overlying paint, which must be estimated. For this reason we prefer to use the ratio of the intensities of the x-rays, as in Equs. 21 or 22 rather than the logarithm of the ratio, as in Equ. 23, for the depth index. We emphasize that the two methods are essentially equivalent.

To illustrate the use and sensitivity of a depth measurement we take the example of NITON's XL lead detector measuring a concentration of lead of 2 mg/cm², which is twice the HUD guideline for acceptable lead concentration. If the lead paint is on or very close to the surface of an architectural structure such as a wall, then the intensity of the $L_\alpha$ and $L_\beta$ x-rays in the XL will each be about 400 counts per second; that is, the $L_\alpha$ and $L_\beta$ peaks will have equal strengths and will stand very clearly above the background of about 30 counts per second.

Consider the results of a measurement in which the 2 mg/cm² of lead paint is beneath 4 coats of typical $TiO_2$ based paint containing about 20% $TiO_2$; the total thickness, t, of the overlaying paint being 0.03 cm. The density of the overlaying paint will be approximately 1.6 g/cm³ and the mass absorption coefficients for the 10.5 keV, $L_\alpha$ x-ray and the 12.6 keV, $L_\beta$ x-ray will be 30 cm²/g and 18 cm²/g respectively, as determined from Table 1a. The observed intensity of the 10.5 keV line will be 95 counts per second and the observed intensity of the 12.6 keV line will be 168 counts per second. The ratio of the intensity of the 12.6 keV to the 10.5 keV lines will be 168/95=1.8 rather than 1.0 as was the case when the lead paint was on the surface. The ratio 1.8, which can be measured to an uncertainty of about 10% in 4 seconds, is a qualitative index of the fact that the lead is buried beneath about 0.3 mm of non-lead paint. More quantitative indices are given by $D_{cover}$, of Equ. 21 or $d_{cover}$ of Equ. 22, which yield values, in this example, of 2.6 and 2.9 respectively.

If the 2 mg/cm² of lead is covered by only 2 coats of the $TiO_2$ based paint, then the ratio of the intensities of the 12.6 keV to the 10.5 keV peaks would be 1.3 and $D_{cover}$ and $d_{cover}$ would be 1.6 and 1.7 respectively. If the 2 mg/cm² of lead is covered by 8 coats of the $TiO_2$ based paint, then the ratio of the intensities of the 12.6 keV to the 10.5 keV peaks would be 3.2 and $D_{cover}$ and $d_{cover}$ would be 6.7 and 8.4 respectively.

How thick an overlying, good integrity layer of non-lead paint might be considered safe has not yet been determined but this invention gives the inspectors a quantitative gage to tell that the lead is on or near the surface or is buried by several or many layers of non-lead paint.

We note that while we have described the measure of the cover thickness in terms of $L_\alpha$ and $L_\beta$, we could have derived analogous measures in terms of the intensities of any two of the three L lines of lead.

We claim:

1. A method for measuring the absorption of a covering layer that lies on top of a target element capable of emitting $L_\alpha$ and $L_\beta$ x-rays when suitably excited by an appropriate excitation radiation, said layers of covering material do not contain the target element, comprising the steps of: inducing $L_\alpha$ and $L_\beta$ x-rays from said target element by means of said appropriate excitation radiation means so that the $L_\alpha$ and $L_\beta$ x-rays are emitted through said covering layer, detecting said $L_\alpha$ and $L_{62}$ x-rays with a detector having sufficient energy resolution to measure the intensity of the $L_\alpha$ and $L_\beta$ x-rays separately, using the measured intensities of the $L_\alpha$ and $L_\beta$ x-rays to calculate the absorption of the $L_\beta$ x-rays by said covering layer by means of the following equation, $$\frac{1}{a(\beta)} = \left[\frac{P(\beta)\epsilon(\beta)I(L_\beta)}{P(\alpha)\epsilon(\alpha)I(L_\alpha)}\right]^{1/(R_1-1)}$$

where $a(\beta)$ is said absorption of the $L_\beta$ x-rays produced by the said covering material, $P(\beta)$ and $P(\alpha)$ are the probabilities for exciting the $L_\beta$ and $L_\alpha$ x-rays, respectively, by said excitation radiation means, $\epsilon(\beta)$ and $\epsilon(\alpha)$ are the efficiencies for detecting the $L_\beta$ and $L_\alpha$ x-rays by said detector, $I(L_\beta)$ and $I(L_\alpha)$ are the measured intensities of the $L_\beta$ and $L_\alpha$ x-rays respectively, induced from said target element, and $R_1$, the ratio of the mass attenuation coefficient for the $L_\beta$ to that of the $L_\alpha$ x-rays, is a constant that is essentially independent of the nature of said covering layer.

2. A method for obtaining a quantitative index of the thickness of a covering layer that lies on top of a target element capable of emitting $L_\alpha$ and $L_\beta$ x-rays when suitably excited by an appropriate excitation radiation, said layers of covering material do not contain the target element, comprising the steps of: inducing $L_\alpha$ and $L_\beta$ x-rays from said target element by means of said appropriate excitation radiation means so that the $L_\alpha$ and $L_\beta$ x-rays are emitted through said covering layer, detecting said $L_\alpha$ and $L_\beta$ x-rays with a detector having sufficient energy resolution to measure the intensity of the $L_\alpha$ and $L_\beta$ x-rays separately, using the measured intensities of the $L_\alpha$ and $L_\beta$ x-rays to determine a depth index $D_{cover}$ by means of the following equation, $$D_{cover} = \left[ \frac{I(L_\beta)/I(L_\alpha)}{(I(L_\beta)/I(L_\alpha))_{stand}} \right]^{1/(R_1-1)}$$

where $I(L_\beta)/I(L_\alpha)$ is the ratio of the measured intensity of the $L_\beta$ to that of the $L_\alpha$ x-rays from said target element, $(I(L_\beta)/I(L_\alpha))_{stand}$ is the ratio of the measured intensity of the $L_\beta$ to that of the $L_\alpha$ x-rays from a standard of the target element placed in the same position as said target element, and $R_1$, the ratio of the mass attenuation coefficient for the $L_\beta$ to that of the $L_\alpha$ x-rays, is a constant that is essentially independent of the nature of said covering layer.

3. The method according to claim 1 in which the target element is a lead-based paint and the covering layers do not contain lead.

4. The method according to claim 2 in which the target element is a lead-based paint and the covering layers do not contain lead.

5. A device for measuring the absorption power of layers of material that cover a target element, said covering material not containing the target element, comprising: a source means of photons, with energies at least greater than the L binding energy of said target element, that will induce or fluoresce the $L_\alpha$ and $L_\beta$ x-rays from the target, a detector means to measure the intensity distribution of the spectrum of photons emitted from surface containing said target element, said detector means having sufficient energy resolution to separately measure the $L_\alpha$ and $L_\beta$ x-rays emitted from said target element, a radiation shield means to isolate said detector from the direct radiations from said source of photons, an output means to record and display the deduced value of the absorption of said $L_\beta$ (or $L_\alpha$ x-rays) target element, the device including an electronic/computer means for determining the absorption of the $L_b$ x-rays by said covering layers by means of the equation, $$\frac{1}{a(\beta)} = \left[ \frac{P(\beta)\epsilon(\beta)I(L_\beta)}{P(\alpha)\epsilon(\alpha)I(L_\alpha)} \right]^{1/(R_1-1)}$$

where $a(\beta)$ is said absorption of the $L_\beta$ x-rays produced by the said covering material, $P(\beta)$ and $P(\alpha)$ are the probabilities for exciting the $L_\beta$ and $L_\alpha$ x-rays, respectively, by said excitation radiation means, $\epsilon(\beta)$ and $\epsilon(\alpha)$ are the efficiencies for detecting the $L_\beta$ and $L_\alpha$ x-rays by said detector, $I(L_\beta)$ and $I(L_\alpha)$ are the measured intensities of the $L_\beta$ and $L_\alpha$ x-rays respectively, induced from said target element, and $R_1$, the ratio of the mass attenuation coefficient for the $L_\beta$ to that of the $L_\alpha$ x-rays, is a constant that is essentially independent of the nature of said covering layer.

6. A device for obtaining an index of the absorption power of layers of material that cover a target element, said covering material not containing the target element, comprising: a source means of photons, with energies at least greater than the L binding energy of said target element, that will induce or fluoresce the $L_\alpha$ and $L_\beta$ x-rays from the target, a detector means to measure the intensity distribution of the spectrum of photons emitted from surface containing said target element, said detector means having sufficient energy resolution to separately measure the $L_\alpha$ and $L_\beta$ x-rays emitted from said target element, a radiation shield means to isolate said detector from the direct radiations from said source of photons, an output means to record and display the deduced value of the index of absorption of said $L_\beta$ (or $L_\alpha$ x-rays) target element, the device including an electronic/computer means for determining the index of absorption of the $L_b$ x-rays by said covering layers by means of the equation, $$D_{cover} = \left[ \frac{I(L_\beta)/I(L_\alpha)}{(I(L_\beta)/I(L_\alpha))_{stand}} \right]^{1/(R_1-1)}$$

where $I(L_\beta)/I(L_\alpha)$ is the ratio of the measured intensity of the $L_\beta$ to that of the $L_\alpha$ x-rays from said target element, $(I(L_\beta)/I(L_\alpha))_{stand}$ is the ratio of the measured intensity of the $L_\beta$ to that of the $L_\alpha$ x-rays from a standard of the target element placed in the same position as said target element, and $R_1$, the ratio of the mass attenuation coefficient for the $L_\beta$ to that of the $L_\alpha$ x-rays, is a constant that is essentially independent of the nature of said covering layer.

7. A device for obtaining an index of the absorption power of layers of material that cover a target element, said covering material not containing the target element, comprising: a source means of photons, with energies at least greater than the L binding energy of said target element, that will induce or fluoresce the $L_\alpha$ and $L_\beta$ x-rays from the target, a detector means to measure the intensity distribution of the spectrum of photons emitted from surface containing said target element, said detector means having sufficient energy resolution to separately measure the $L_\alpha$ and $L_\beta$ x-rays emitted from said target element, a radiation shield means to isolate said detector from the direct radiations from said source of photons, an output means to record and display the deduced value of the index of absorption of said $L_\beta$ (or $L_\alpha$ x-rays) target element, the device including an electronic/computer means for determining the index of absorption of the $L_b$ x-rays by said covering layers by means of the equation, $$D_{cover} = \frac{I(L_\beta)/I(L_\alpha)}{(I(L_\beta)/I(L_\alpha))_{stand}}$$

where $I(L_\beta)/I(L_\alpha)$ is the ratio of the measured intensity of the $L_\beta$ to that of the $L_\alpha$ x-rays from said target element and $(I(L_\beta)/I(L_\alpha))_{stand}$ is the ratio of the measured intensity of the $L_\beta$ to that of the $L_\alpha$ x-rays from a standard of the target element placed in the same position as said target element, the value of $D_{cover}$ increasing from unity as the thickness of said covering layer increases.

\* \* \* \* \*